(12) United States Patent
Sakai et al.

(10) Patent No.: US 7,020,350 B2
(45) Date of Patent: Mar. 28, 2006

(54) IMAGE ALIGNMENT METHOD, COMPARATIVE INSPECTION METHOD, AND COMPARATIVE INSPECTION DEVICE FOR COMPARATIVE INSPECTIONS

(75) Inventors: Kaoru Sakai, Yokohama (JP); Shunji Maeda, Yokohama (JP); Takafumi Okabe, Yokohama (JP)

(73) Assignee: Hitachi, Ltd., Tokyo (JP)

( * ) Notice: Subject to any disclaimer, the term of this patent is extended or adjusted under 35 U.S.C. 154(b) by 744 days.

(21) Appl. No.: 09/802,687

(22) Filed: Mar. 8, 2001

(65) Prior Publication Data

US 2001/0053245 A1 Dec. 20, 2001

(30) Foreign Application Priority Data

Jun. 15, 2000 (JP) ........................................ 2000-184563

(51) Int. Cl.
*G06K 9/32* (2006.01)

(52) U.S. Cl. ........................ 382/294; 382/141; 382/149; 382/151; 382/284; 358/540; 358/450

(58) Field of Classification Search ................. 382/141, 382/143, 145, 149, 151, 218, 278, 284, 294, 382/147, 209; 358/540, 448, 450, 452, 598, 358/474, 488
See application file for complete search history.

(56) References Cited

U.S. PATENT DOCUMENTS

| | | | | |
|---|---|---|---|---|
| 4,702,606 A | * | 10/1987 | Matsuura et al. | ............ 356/401 |
| 4,742,376 A | * | 5/1988 | Phillips | ........................ 355/77 |
| 4,805,123 A | | 2/1989 | Specht et al. | |
| 5,792,580 A | * | 8/1998 | Tomimatu | ..................... 430/22 |
| 5,923,403 A | * | 7/1999 | Jain | ............................ 355/26 |
| 6,097,473 A | * | 8/2000 | Ota et al. | ..................... 355/53 |
| 6,700,667 B1 | * | 3/2004 | Nishi | ......................... 356/509 |

OTHER PUBLICATIONS

Yoda Haruo et al., "Inspecting Apparatus for Defect of Repeated Pattern," Japanese Patent Abstract, 05–264467, Dec. 10, 1993, p. 1.

* cited by examiner

*Primary Examiner*—Yon J. Couso
*Assistant Examiner*—Yosef Kassa
(74) *Attorney, Agent, or Firm*—Townsend and Townsend and Crew LLP

(57) ABSTRACT

The present invention provides a high-precision alignment method, device and code for inspections that compare an inspection image with a reference image and detect defects from their differences. In one embodiment an inspection image and a reference image are divided into multiple regions. An offset is calculated for each pair of regions. Out of these multiple offsets, only the offsets with high reliability are used to determine an offset for the entire image. This allows high-precision alignment with little or no dependency on pattern density or shape, differences in luminance between images, and uneven luminance within individual images. Also, detection sensitivity is adjusted as necessary by monitoring alignment precision.

20 Claims, 11 Drawing Sheets

FIG.12
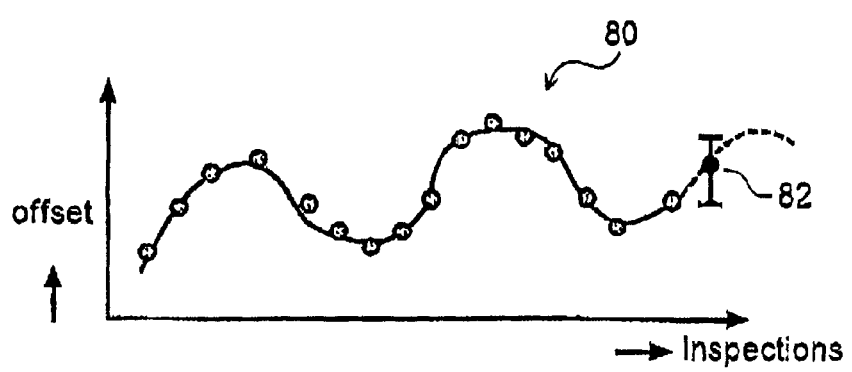
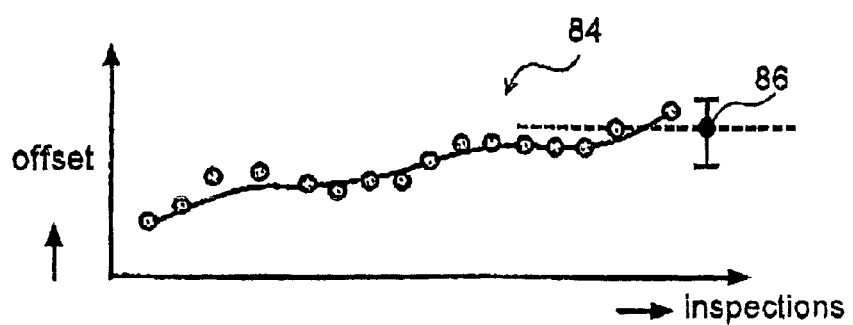

IMAGE ALIGNMENT METHOD, COMPARATIVE INSPECTION METHOD, AND COMPARATIVE INSPECTION DEVICE FOR COMPARATIVE INSPECTIONS

CROSS-REFERENCES TO RELATED APPLICATIONS

This application is related to and claims priority from Japanese Patent Application No 2000-184563, filed on Jun. 15, 2000.

BACKGROUND OF THE INVENTION

Japanese laid-open patent publication number Hei 05-264467 describes a known pattern inspection method in which defects are detected by comparing an inspection image and a reference image.

In this method, a line sensor sequentially images an inspected object on which a repeated pattern is arranged in an orderly manner. A comparison is made with an image that has been delayed by a time interval corresponding to the pitch of the repeated pattern, and inconsistencies are detected as pattern defects. However, in practice the stage may vibrate or the inspected object may be tilted so that the two images are not always aligned. Thus, an offset must be determined for the image that has been delayed by the pitch of the repeated pattern. The two images are then aligned based on the determined offset. Then, differences between the images, e.g., luminance differences, are determined. If a difference is greater than a defined threshold value, it is determined to be a defect. Otherwise, it is determined to not be defective.

A standard alignment method for two images is an alignment method where the information from each of the full images are used to calculate an offset all at once. Problems related to this standard method are illustrated by FIGS. 1 and 2. FIG. 1 shows front-view drawings of examples of full images 110, 112, and 114 that tend to lead to failed alignments. FIG. 2 shows front-view drawings of examples of detection results 120, 122, 124 for full images that have failed alignments.

In comparative inspections, alignment of two full images is generally performed by using edges within the images as information for offset detection. An offset is calculated so that the edge offsets between the full images are minimized. There can be cases, as in FIG. 1 image 110 where there is only an elliptical pattern 21 at the right end of the image, in which there is very little edge information, i.e., the proportion of edges relative to the entire alignment region (hereinafter referred to as pattern density) is very low. There are other cases, as in FIG. 1 image 112 where there are many vertical edges 22 but there is only a rectangular pattern 23 oriented horizontally, in which edges are predominantly in a specific direction. There are other cases, as in FIG. 1 image 114 where there are many very small circular patterns 24 with only one black dot 25, in which a fine-pitch pattern dominates. In all of these cases, there is a high probability that an offset calculation error will be generated. Thus, methods that calculate offsets based on the information for entire images, as in the conventional technology, have a high probability that erroneous detections (false positives) will be generated by the offset.

The detection results from full images, such as in FIG. 1, with failed offsets are shown in FIG. 2 and will generate erroneous detections. FIG. 2 images 120, 122, 124 show erroneous detection positions 31, 32, 33, 34, 35. Furthermore, the possibility of errors is increased even more if there is luminance shading within an image or if there is uneven brightness between images. One method of reducing erroneous detections due to alignment is to lower the sensitivity. However, not all alignment errors cause a false detection. In addition lowering the sensitivity, lowers the detection rate for true defects. Thus unnecessary lowering of the sensitivity due to alignment errors should be avoided.

Thus there is a need for improved alignment techniques in which detection errors are minimally caused by alignment errors due to pattern density or shape, and/or for improved techniques for determining when the detection sensitivity needs to be lowered in comparison inspections.

SUMMARY OF THE INVENTION

The present invention provides a high-precision alignment method, device and code for inspections that compare an inspection image with a reference image and detect defects from their differences. In an embodiment an inspection image and a reference image are divided into multiple regions. An offset is calculated for each pair of sub-images. Out of these multiple offsets, only the offsets with high reliability are used to determine an offset for the entire image. This allows high-precision alignment with little or no dependency on pattern density or shape, differences in luminance between images, and uneven luminance within individual images. Also, detection sensitivity is adjusted as necessary by monitoring alignment precision. One embodiment of the present invention is suited for use in an alignment method implemented for visual inspection of semiconductor wafers. Other embodiments include use of a Semiconductor Electron Microscope, X-ray system, Focus Ion beam, Transparent Electron Microscope, and the like.

A second embodiment of the present invention provides a comparative inspection device including: a stage on which an object is mounted and which moves the object; a detector detecting an image of the object, the image including a plurality of small inspection image regions, and outputting an image signal; and an image processing unit for determining offsets for the inspection image regions when compared with corresponding reference image regions, and for determining an offset having a high reliability out of the offsets for the inspection image regions. The offset with high reliability is used to align an entire inspection image and an entire reference image.

In the second embodiment, the reliability for a small region can be evaluated as being a high reliability, if patterns in the small region are dense and can be evaluated as being a low reliability, if the patterns are sparse. Also, the full image reliability can be evaluated by comparison with an offset predicted from past variations of offsets.

A third embodiment of the present invention provides a method for aligning comparative inspection images including the following steps: an image detection step detecting an image of an object, the image having a plurality of inspection images of small regions, and outputting an image signal; an offset determining step determining offsets for the plurality of inspection images; an offset selection step selecting an offset with a high reliability; and a step for aligning an entire inspection image and an entire reference image using the offset with high reliability.

A forth embodiment of the present invention provides a method for aligning two images by comparing an inspection image and a reference image. When the inspection image and the reference image are compared and aligned, each of the two received images is divided into a plurality of regions, offsets are calculated for corresponding divided images, and an offset for an entire image is determined from a plurality of calculated offsets. In an alternate embodiment, when determining an offset for the entire image using the plurality of calculated offsets, the offset for the entire image is determined using only offsets with high reliability. Also, when images are received consecutively, reliability of the determined offset for the entire image is evaluated and, if the reliability is low, the entire image is aligned using a past offset having a high reliability. Also, when images are received consecutively, if an evaluation of reliability for the determined offset determines that reliability is high, the offset for a current image is stored as reference data for subsequent alignments. Also, when images are received consecutively and offset reliability is to be evaluated, past offsets with high reliability are collected and these are compared with a current image offset to determined reliability.

A fifth embodiment of the present invention provides a method for comparative inspection including the following steps: a step for dividing an inspection image into a plurality of regions; a step for dividing a reference image into a plurality of regions; a step for calculating offsets between corresponding inspection images and reference images; a step for determining an offset for an entire image by using only offsets with high reliability selected from offsets calculated for divided images; a step for evaluating reliability of the offset that was finally determined; and a step for adjusting detection sensitivity based on the finally determined evaluation result when detecting defects through image comparison.

Alternatively, the fifth embodiment can also include a step for aligning entire images using a past offset with high reliability if the determined offset for the entire image has a low reliability. Alternatively, there can also be a step for evaluating whether or not an alignment error is critical or not for an image to which the finally determined offset is applied and a step for adjusting detection sensitivity based on the reliability evaluation result and the criticality evaluation result.

A sixth embodiment of the present invention provides a comparative inspection device including means for dividing and inputting two images to be processed; means for simultaneously calculating offsets for individual images input in a divided manner; means for evaluating reliability of offsets calculated for each divided image and calculating an offset for an entire image based on offsets having high reliability; means for evaluating reliability of the calculated offset for the entire image and using the evaluation to determine a final offset; means for aligning the divided images using the final offset; means for monitoring alignment precision; means for adjusting detection sensitivity based on monitoring results; and means for outputting inspection results along with detection sensitivity. Alternatively, the means for inputting the images includes a stage moving an inspected object, an illumination source illuminating the inspected object, a sensor imaging the inspected object and outputting the image as a plurality of divided regions, an A/D converter circuit digitizing an output signal from the sensor, and a memory for storing this; and the offset calculating means includes an arithmetic module simultaneously calculating offsets from image data stored in the memory as a plurality of divided images.

A seventh embodiment of the present invention provides a computer program product stored on a computer readable medium for aligning a first image having a circuit pattern in a semiconductor material with a second image. The computer program product includes: code for dividing the first image into a plurality of regions; code for dividing the second image into a corresponding plurality of regions; code for determining a first region offset of a first region of said plurality of regions from a first corresponding region of the corresponding plurality of regions; and code for using the first region offset in determining an image offset for the first image.

These and other embodiments of the present invention are described in more detail in conjunction with the text below and attached figures.

BRIEF DESCRIPTION OF THE DRAWINGS

FIGS. 12 show curves which track the variations in offsets in the comparative inspection device of an embodiment of the present invention.

DESCRIPTION OF THE SPECIFIC EMBODIMENTS

The following is a description of the embodiments of the present invention, with references to the figures.

Figure 1:
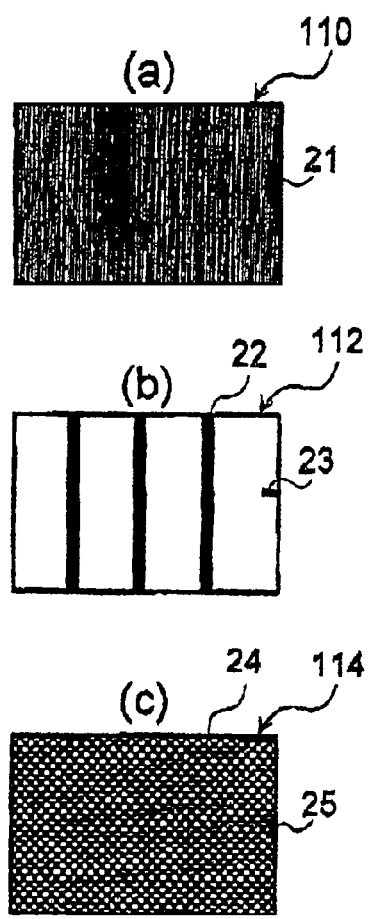
FIG. 1 shows examples of front-view drawings of images that tend to lead to failed alignment.
Figure 2:
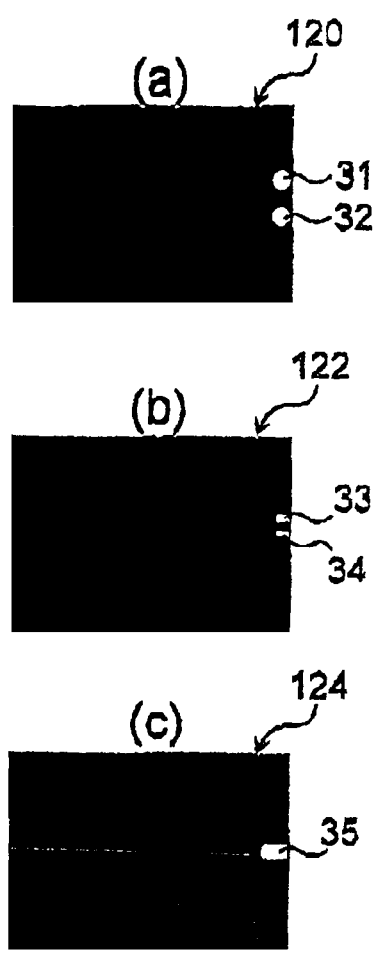
FIG. 2 shows examples of front-view drawings of detection results for images that lead to failed alignment.

In the case of detecting misalignment between an image to be inspected, i.e., inspection image, and a reference image, the positional displacement or offset of the inspection image from the reference image is calculated so as to minimize the displacement of the edges between the images. However, as shown in FIG. 1 above there are several cases where there is a high probability of error in the offset calculation. Some of the cases are: 1) the edge density is low; 2) the number of edges in a specified direction is high, and 3) the number of repetitive patterns of fine pitch is high.

Thus when the prior art method of calculating an amount of positional offset based on information about the entire image is used, there is a high probability of producing a false detection due to an incorrect offset at the location of the irregular pattern.

In order to show the reasons why such incorrect offset calculations occur, an example of detecting a positional displacement between an image to be inspected and a reference image using a correlation matrix is provided for the purposes of illustration.

Figure 3:
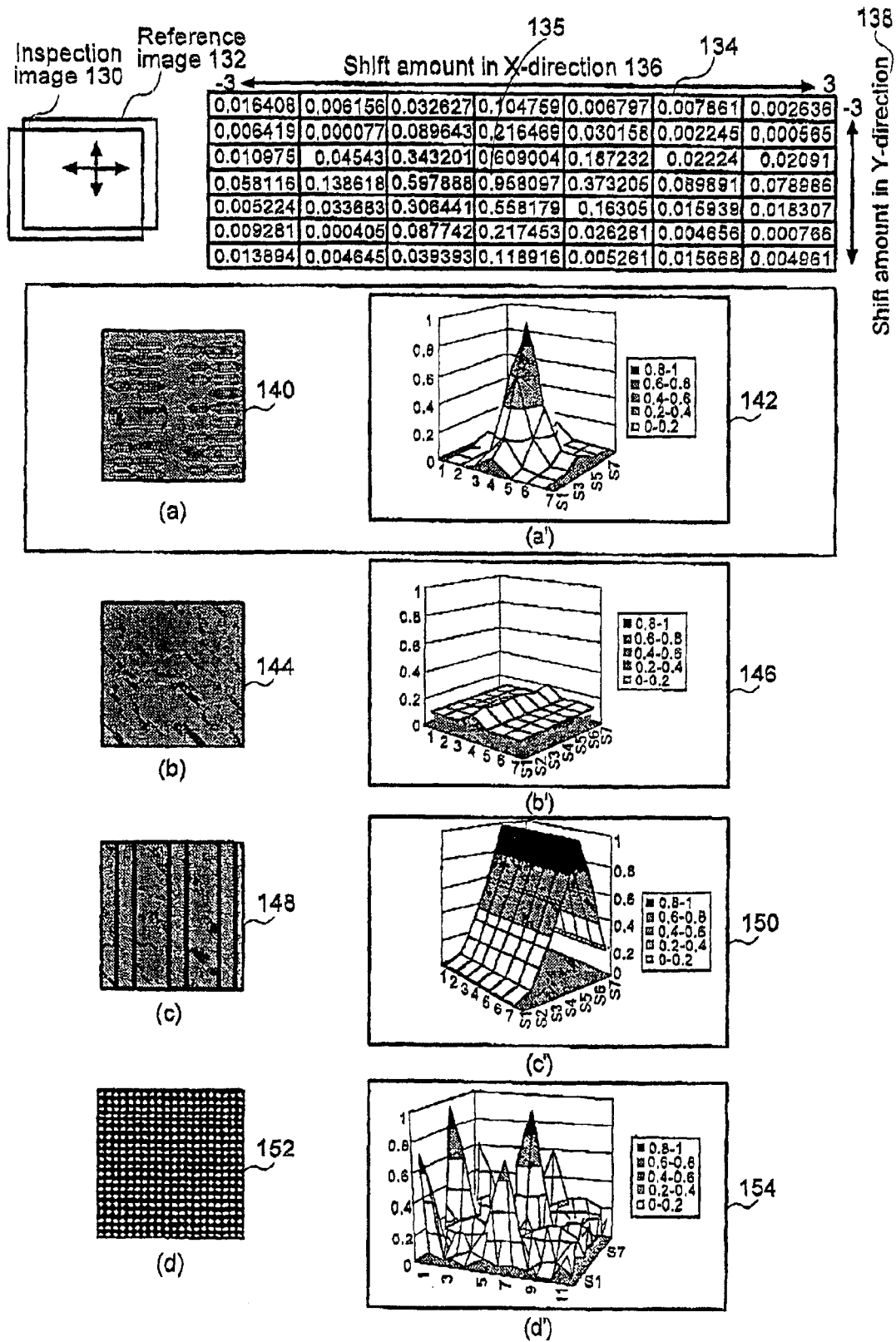
FIG. 3 shows an example of several patterns, a correlation matrix, and three dimensional (3-D) graphs showing distributions of correlation values for the patterns.

FIG. 3 shows an example of several patterns, a correlation matrix, and three dimensional (3-D) graphs showing distributions of correlation values for the patterns. In FIG. 3 an Inspection image 130 overlays a Reference image 132 in order to calculate the correlation matrix. An example correlation matrix is shown as 134 with the center 135 of the matrix 134 indicating zero offset, i.e., the Inspection image 130 is directly over the Reference image 132. More specifically, the two images 130 and 132, where a positional displacement is to be calculated are shifted relatively in a direction of x by −m to +m pixels and in a direction of y by −i to +i pixels. For each shift a correlation value is calculated and the value is entered in a correlation matrix with the position in the matrix given by the x, y shift. The number of matrix elements is: $M=((2*m+1))\times((2*i+1)$. In FIG. 3, it is assumed that $m=i=3$ is applied. For images 130 and 132, a total number of M=49 values are calculated in response to an amount of shift of the image 140 over itself. Then, an amount of shift when the value becomes a maximum value from these correlation values becomes an amount of positional displacement between the images. In Image 140 the correlation matrix is 134 showing the x-direction shift 136 and the y direction shift 138. The maximum value is found at the center 135 (when an amount of shift is 0 in both a direction X and a direction Y), so that an amount of positional displacement of the image 140 becomes 0 pixels in both a direction of X and a direction of Y.

A three dimensional graph showing the x-y offset versus correlation value for 140 (or matrix 134) is shown as graph 142. As can be seen, where there is present a sufficient amount of patterns in the image 140, that is, in the case where a high pattern density is present, the distribution of values as indicated in graph 142 has a single peak that is near 1.0. However, at a location where no pattern is present as indicated in image 144, no peak is present in graph 146 and also its maximum correlation values are also low. In the case where the pattern is present only at a specified direction as indicated in image 148, the correlation values become increased in a direction of the pattern, and a ridge is produced in graph 150. In image 152 a plurality of high peak values are produced on the graph 154 in the case of repetitive dot patterns at a finer pitch than the image shift range. In the cases of patterns as indicated in images 144, 148, and 152, it is hard to find one true peak value.

Thus the above example illustrates that there are cases in which correlation alone over a full image may not be sufficient to determine an offset. However, as shown later by an embodiment of the present invention, correlations plus the use of reliability measurements over portions of a full image allow location of an offset for the image.

Next, a comparative inspection device and misalignment detection method will be described, with references to FIG. 4.

Figure 4:
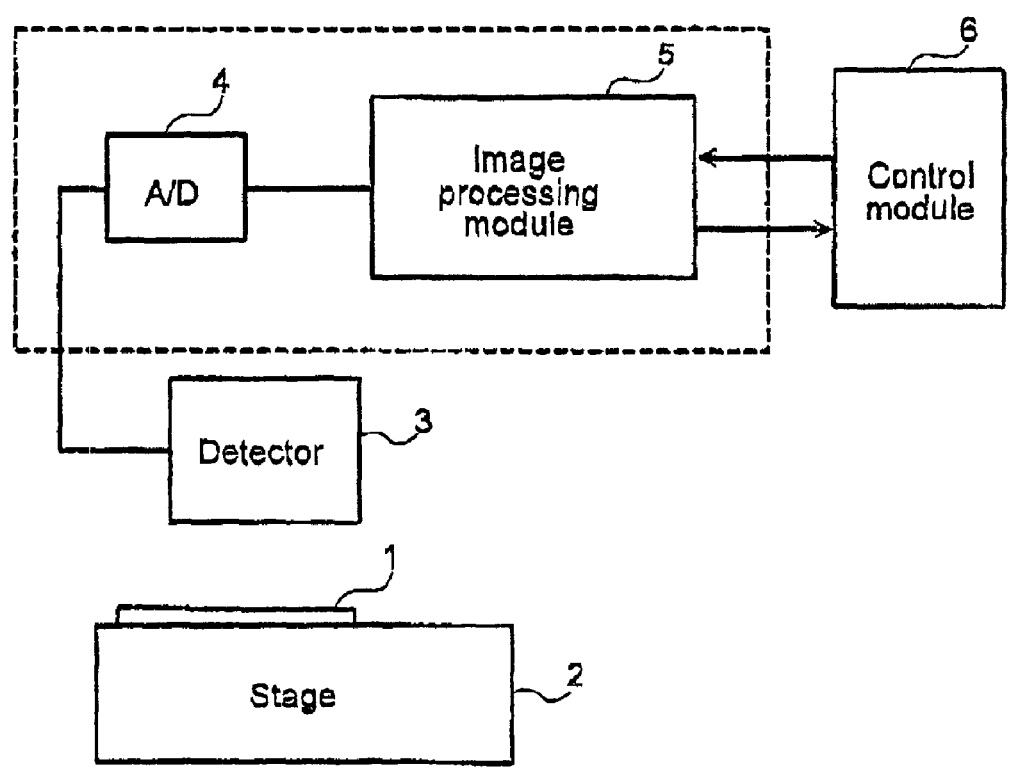
FIG. 4 shows a schematic drawing of an architecture of an embodiment of a comparative inspection device according to the present invention.

FIG. 4 is a schematic drawing of the architecture of an embodiment of a comparative inspection device according to the present invention. A bright field inspection device is used to inspect a semiconductor wafer. In the figure, a semiconductor wafer 1 is the inspected object. The semiconductor wafer 1 is secured to a stage 2, which then moves the semiconductor wafer 1. A detector 3 captures the image of the semiconductor wafer. An A/D converter 4 digitizes the output signal from the detector 3. An image processing module 5 detects defects by comparing two captured images. The figure also shows a general control module 6.

Figure 5:
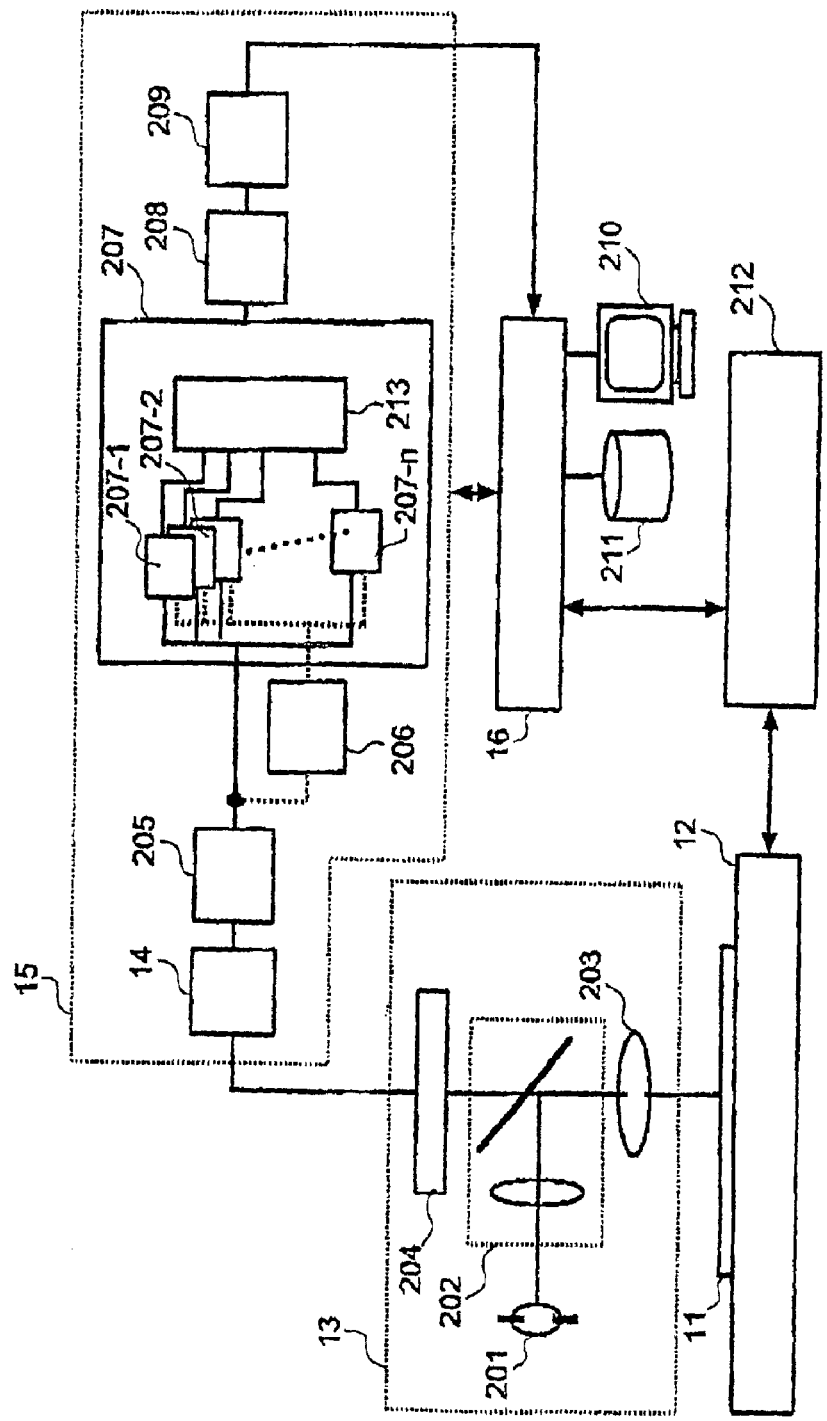
FIG. 5 shows an embodiment of a bright field inspection device of the present invention.

FIG. 5 shows an embodiment of a bright field inspection device of the present invention. Item 11 denotes a specimen to be inspected such as a semiconductor wafer; 12 denotes a stage for mounting the item 11 to be inspected and for moving the item 11; 13 denotes a sensing unit. This apparatus includes a light source 201 for irradiating the item to be inspected 11; an illuminating optical system 202 for condensing light irradiated from the light source 201; an objective lens 203 for imaging an optical image obtained by irradiating the item 11 to be inspected with irradiating light condensed by the illuminating optical system and reflecting the illuminated light from the item to be inspected; and an image sensor 204 for receiving the imaged optical image and converting it into an image signal corresponding to brightness. 15 denotes an image processing unit for calculating a defect candidate in the item 11 in reference to an image detected by the sensing unit 13. The image processing unit 15 includes an A/D converter 14 for converting an input signal from the sensing unit 13 into a digital signal; a pre-processing unit 205 for performing image corrections such as a shading correction and a dark level correction or the like with the digital signal; a delay memory 206 for storing a digital signal of the previous chip as a reference image signal; a positional displacement detecting unit 207 for detecting a positional displacement between a digital signal (an inspection image signal) detected by the sensing unit 13 and the reference image signal of the delay memory 206; an image comparing section 208 for performing a positional alignment between the detected image, i.e., inspection image, and the reference image by application of the calculated positional displacement amount. Section 208 also compares both image signals and outputs a part where a non-coincidence portion is larger than a specified threshold value as a defect candidate; and a feature extracting section 209 for calculating the coordinates of defect candidate or an amount of feature or the like. 16 denotes an entire control section comprised of a user-interface section 210 having a display means and an input means for accepting a variation of inspection parameters (threshold values applied in the image comparison) from a user or displaying detected defect information; a memory device 211 for storing feature s of detected defect candidates or images and the like; and a CPU for performing various kinds of controls. 212 denotes a mechanical controller for driving the stage 12 in response to a control instruction from the control section 16. Further, the image processing unit 15 and the sensing unit 13 and the like are also driven by instructions from the control section 16.

In one embodiment the positional displacement detecting unit 207 divides each inputted inspection image and reference image into a number of (n) regions. The positional displacement or offset calculations are carried out for every region. 207-1, 207-2, . . . 207-n denote positional displacement calculating units in the n channels for calculating in parallel, positional displacements for each of the region sets (a region set includes a region of an inspection image and a region of a corresponding reference image). 213 denotes a CPU for sensing a positional displacement or offset for the entire image based on the "n" positional displacement amounts determined by the positional displacement calculation units.

Figure 6:
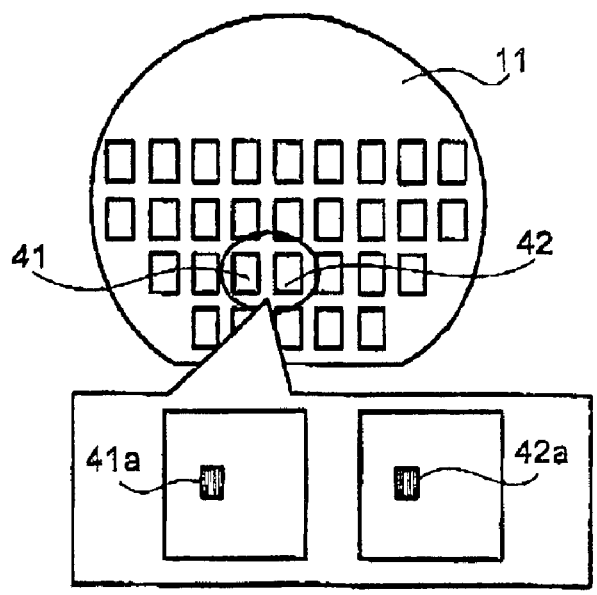
FIG. 6 shows an example of a front-view drawing of a region on a chip to be aligned.

As shown in the front-view drawing in FIG. 6, the inspected semiconductor wafer 11 is formed with multiple identically patterned chips 41, 42 arranged in an orderly manner. In one embodiment of the inspection device in FIG. 5, images of identical positions on two chips, e.g., areas 41a, 42a on the chips 41, 42 in FIG. 6, are compared and differences are detected as defects. The following is a description of this operation. The general control module 16 moves the semiconductor wafer 11 continuously using the stage 12. In tandem with this, the detector 13 captures chip images. The sensor 204 in the detector 13 is divided into multiple sensor channels along the direction perpendicular to the direction in which the stage moves. For example, the sensor may include 32 parallel sensor channels, where each sensor channel has 128 sensing elements. The incoming signal is sent to the A/D converter 14 as multiple sub-signals. The A/D converter 14 converts the analog signal divided into multiple signals into a digital signal, which is sent to the pre-processing unit 205 of image processing unit 15. The delay memory 206 is used so that an image signal that has been delayed by an interval corresponding to one chip's worth of movement in the stage 12, i.e., the image signal of the chip previous to the one that is currently set up for inspection, is sent to positional displacement unit 207 together with the image signal of the current chip.

Figure 7:
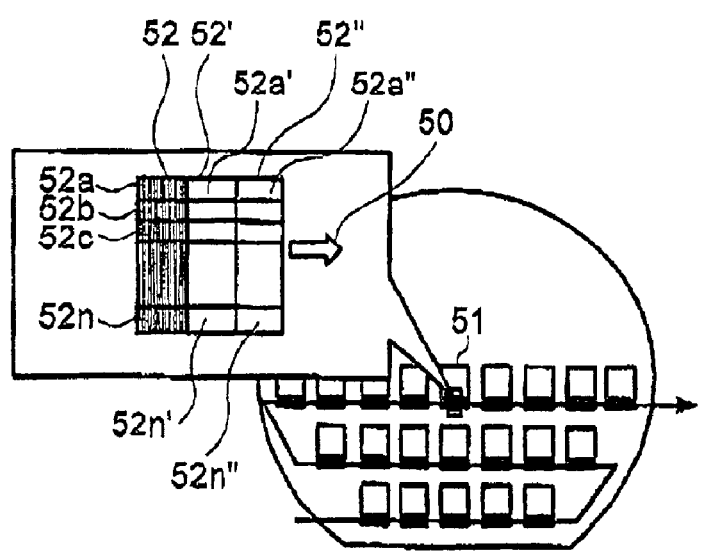
FIG. 7 shows a front-view drawing showing a sample image received by the image processing unit of the comparative inspection device according to an embodiment of the present invention.

FIG. 7 is a front-view drawing showing a sample image 52 received by the image processing unit 15 of the comparative inspection device according to an embodiment of the present invention. An image 52 of a specific area of chip 51 is made up of a plurality of regions 52a, 52b, 52c, ..., 52n. The plurality of regions are sent in parallel to the image processing unit 15 from sensing unit, i.e., detector, 13. For example, region 52a is sent to positional displacement calculating unit 207-1, region 52b is sent to positional displacement calculating unit 207-2, and region 52n is sent to positional displacement calculating unit 207-n. The plurality of regions are also sent to delay memory 206 for use as reference when the next chip is inspected. In the positional displacement calculating units, each 52 region (inspection region) is compared with the stored 52 region (reference region) from a previous chip. For example the region 52a (inspection region) is compared with a previous 52a (reference region) stored in delay memory 206 in positional displacement calculating unit 207-1 and an offset determined. The same procedure is done for 52b which is asynchronously used in positional displacement calculating unit 207-2. Next detector 13 inputs image 52' which includes regions, 52a', 52b', 52c', ..., 52n'. These 52' regions are sent to positional displacement calculating units in the image processing unit 15 and stored in delay memory 206. And the above process for regions 52 is repeated for regions 52'. The image signals of the two chips, sent in succession as the stage 12 is moved, will not correspond to precisely identical positions if the stage vibrates or if the wafer set on the stage is tilted. Thus, the offset between the two successively received images must be calculated and the images must be aligned before performing comparative inspection.

Next, an example of a method for detecting offsets used by the image processing unit 15 will be described, with references to FIG. 8.

Figure 8:
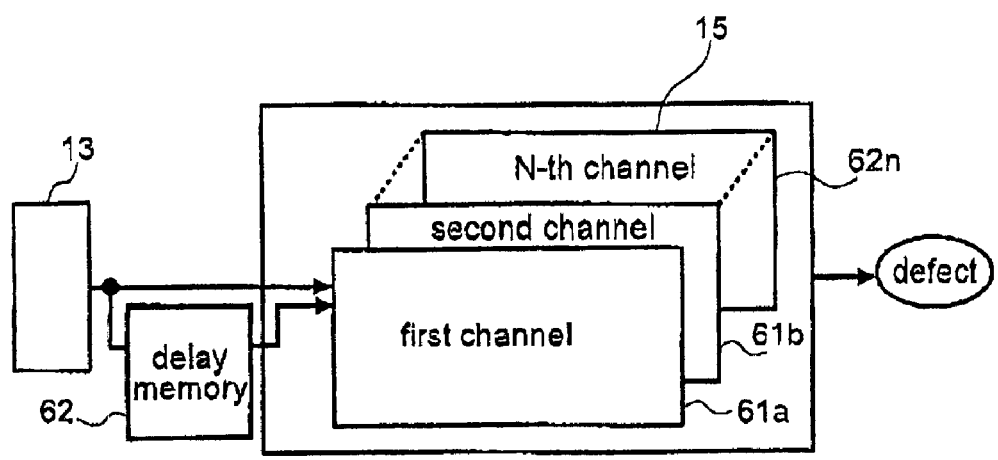
FIG. 8 shows a schematic diagram describing operations performed by the image processing unit of the comparative inspection device according to an embodiment of the present invention.

FIG. 8 is a schematic diagram for the purpose of describing operations performed by the image processing unit of the comparative inspection device according to an embodiment of the present invention. In this example, an bright field inspection device is used. As shown in FIG. 8, the image signal for the current chip, received from the detector 13, and the image signal of the chip detected previously, received from the delay memory 62, are divided into one or multiple sections (in this example, N sections are assumed). These sections are processed in parallel. For example, the area 52 to be detected in a chip is divided up into regions 52a, 52b, ..., 52n, which are detected by the detector 13 and sent to the image processing unit 15. Thus, in this embodiment the incoming image has as the processing unit fixed-size images divided up along lines parallel to the direction in which the stage 12 moves. For example in FIG. 7 the stage is illustrated to move in the direction 50. The images are detected in time order of 52, then 52', 52" and so on. Since each image is made up of regions, region 52a is sent to the first processing system or first channel 61a, then after region 52a is processed, region 52a' is next sent to the first channel 61a and so forth. The processing systems for the images of the regions 52a, 52b, ..., 52n are referred to as channels. In FIG. 8, for example, the image of the region 52a along with the image of the corresponding region of the previous image delayed by a delay memory 62 are processed together by a first channel 61a. The image of the region 52b along with the image of the corresponding region of the previous image delayed by the delay memory 62 are processed together by a second channel 61b. The image of the region 52n along with the image of the corresponding region of the previous image delayed by the delay memory 62 are processed together by an n-th channel 61n.

There are various methods that can be used to calculate offsets. In this case, FIG. 9 will be used to describe a method that calculates offsets through normalized cross-correlations.

Figure 9:
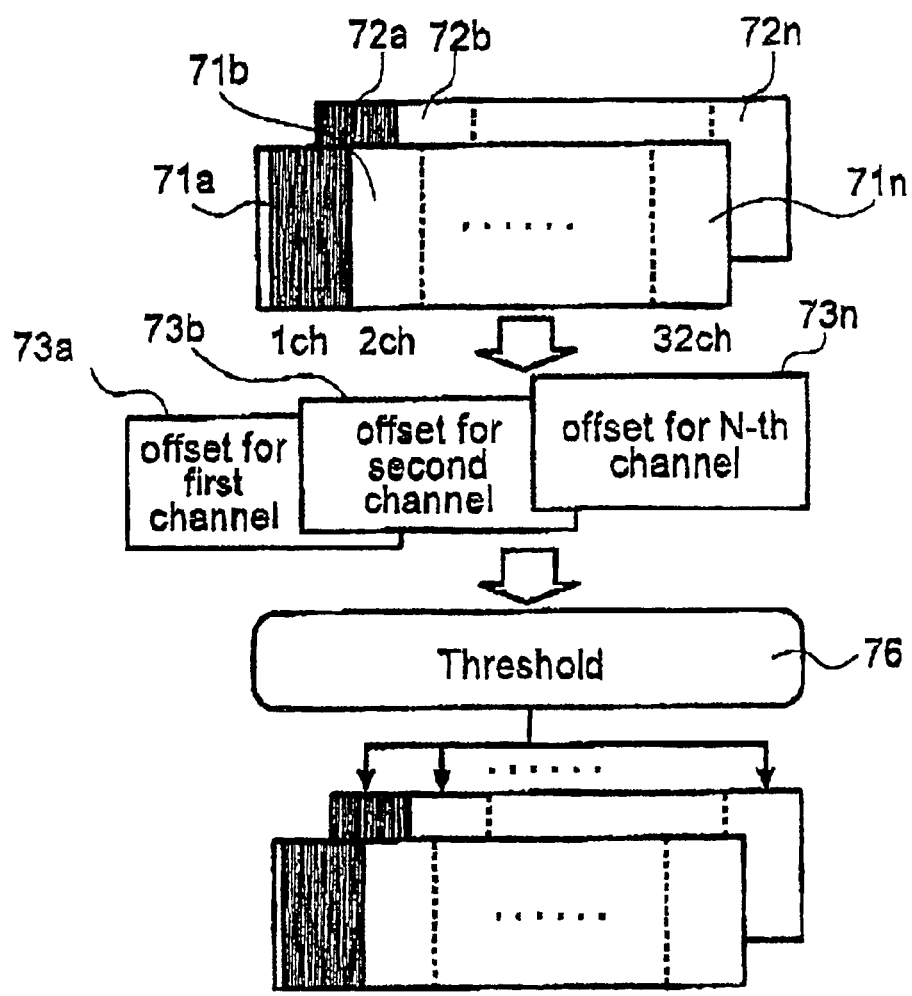
FIG. 9 shows a schematic drawing describing a technique for calculating offsets according to an embodiment of the present invention.

FIG. 9 is a schematic diagram for the purpose of describing a method for calculating offsets according to one embodiment of the present invention. In the figure, inspection images 71a, 71b, ..., 71n are the images of the regions 52a, 52b, ..., 52n, respectively. Reference images 72a, 72b, ..., 72n are the corresponding images from the previous chip. The inspection image 71a and the reference image 72a delayed by the delay circuit 62 are sent to the first channel 61a of the image processing unit 15. The inspection image 71b and the reference image 72b delayed by the delay circuit 62 are sent to the second channel 61b of the image processing unit 15. The inspection image 71n and the reference image 72n delayed by the delay circuit 62 are sent to the n-th channel 61n of the image processing unit 15. Then, for each of the channels 61a–61n, the two images are given relative offsets of −m–+m image elements in the x direction and −m–+m image elements in the y direction. A total of M correlations are calculated, where $$M=((2 \times m+1) \times (2 \times m+1))$$

And the x, y position where the maximum correlation value is found for each channel is determined to be the offset for that channel, i.e., 73a, 73b, ... 73n.

For example, let m=3, and let the reference and inspection images for 71b and 72b of channel 2, each be a square of size 128 elements by 128 elements. The reference image is fixed and the correlation calculations are done for an inner square that is (−64+m) to (64−m) (in this case m=3, so the inner square is −61 to 61) in the x-direction and (−64+m) to (64−m) in the y-direction (−61 to 61). The inspection image is 128 by 128 and has the same origin as the reference image. The inspection image is shifted from −3 to 3 elements with respect to the reference image in the x direction, −3 to 3 elements with respect to the reference image in the y direction, and a correlation is calculated for each inner square associated with an offset, including zero offset. The result is a (2m+1)×(2m+1), or in this example a 7×7, matrix of correlation values (M=49) with the center matrix value representing x, y zero offset. The maximum correlation value in the 7×7 matrix is found and the x, y offsets associated with that maximum value is the offset for channel 2, i.e., 73b. The maximum correlation value and corresponding offset are determined for each of the N channels. Correlation values are in the range of −1.0–1.0, with completely identical images resulting in a correlation of 1.0.

In this example, offsets are determined using normalized cross-correlation and evaluating reliability using correlations. However, it would also be possible to use a method involving the total sum of concentration differences between images. In this case, offsets are calculated for each channel and corresponding indexes are set up to evaluate reliability.

Unlike the conventional technology, this embodiment does not calculate offsets by using entire images in the processing unit. As described above, the region 52 is split up into regions 52a–52n and detected to provide inspection images 71a–71n and reference images 72a–72n. These images are used to determine offsets for channels 61a–61n. In other words, offsets are determined for small regions, and an offset for the entire image is determined using only the offsets from the channels having the highest reliability. This allows detection errors caused by bad offsets to be kept below a specified rate regardless of the densities or shapes of patterns. Of course, the ideal detection error rate is 0%, but factors such as imaging conditions can lead to degraded comparison images. In this embodiment, detection errors due to bad offsets are greatly reduced, if not eliminated, regardless of pattern density or shape, and errors can be kept to 10% or less, and in another specific embodiment, 1% or less, even if there is image degradation.

Figure 10:
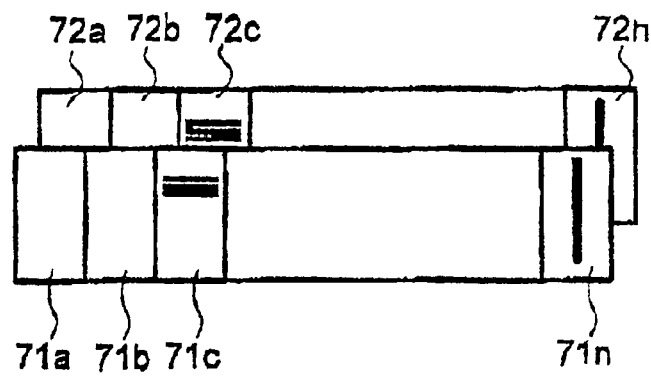
FIG. 10 is a schematic diagram showing an example of images to be processed by one embodiment of the present invention.

FIG. 10 is a schematic diagram showing an example of images to be processed by one embodiment of the present invention. Using these images, the specific advantages of this embodiment will be described. The two images 71, 72 to be inspected have almost no patterns, with only inspection images 71c, 71n and reference images 72c, 72n containing patterns in predetermined directions. These two patterns are formed in different directions.

Figure 11A:
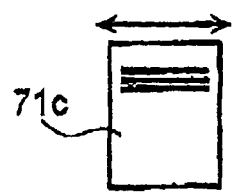
FIGS. 11a to 11d show examples of schematic diagrams describing offsets in sub-images.
Figure 11B:
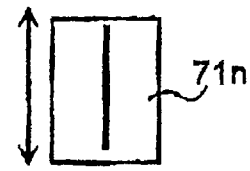

Offset detection is performed primarily using edge information in the conventional method. However, pattern density is extremely low with these types of images, and calculating offsets from entire images as in the conventional technologies can result in a high offset calculation error rate simply from slight brightness shading within images or uneven brightness between images. If offsets are determined for each of the channels 61a–61n and the offset with the highest reliability is selected and applied to all channels, the selected offset will be for the channel 61c or the channel 61n, which are the channels in which the images contain patterns. However, both the channel 61c and the channel 61n contain edges that are predominantly in specific directions. Thus, it is likely that there will be calculation errors in the direction of the arrows shown in FIG. 11a or FIG. 11b relative to the correct offset. This is because there is little edge information in the direction of the arrows. As a result, applying the offset for either the channel 61c or the channel 61n to all channels will generate an offset error in the channel containing the other pattern, leading to a detection error.

Figure 11C:
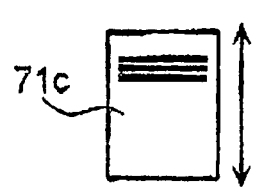
Figure 11D:
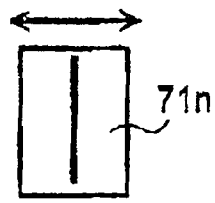

In contrast, with the offset method of this embodiment, the correct offset can be calculated, as will be described below with references to FIG. 11c and FIG. 11d. FIGS. 11a to 11d show schematic diagrams for the purpose of describing offsets in sub-images. This embodiment does not use the offsets for channels with low reliability, such as the channels 61a, 61b that process the empty images 71a, 71b, 72a, 72b, and the like. A composite offset for the entire image is calculated only with the offsets of the channel 61c (not shown) associated with image 71c, and the channel 61n, which contain patterns. Since the offsets of the channel 61c and the channel 61n have high reliability in the directions of the arrows in FIG. 11c and FIG. 11d, the correct offset can be calculated in both the x direction and the y direction by using only the offsets for the directions having high reliability. Note there is a lot of edge information in the direction of the arrows. As a result, detection errors caused by offset errors influenced by pattern density or shapes can be greatly reduced. Also, since statistics needed for determining offsets, e.g., normalized cross-correlation or sums of concentration differences, are calculated within the small regions 52a–52n, the effect of luminance shading within an image and uneven brightness between images is minimized, thus reducing detection errors caused by offset errors.

This embodiment uses only channel information that has high reliability, e.g., out of the images 71a–71n, 72a–72n, only the images with the highest pattern densities. From this, reliability is evaluated for calculated offsets for the entire image. If calculated offsets have low reliability or the calculated offsets from all the channels do not contain a single offset with high reliability, the offset is not determined from the current image. Instead, alignment is performed using the offset from at least one iteration back. For example, if pattern density is extremely low as in the images in FIG. 10, or if an offset with high reliability cannot be found for any of the channels, this embodiment refers to a past offset from images having adequate pattern densities and uses that offset. Conversely, if the current alignment image contains adequate pattern density and the calculated offset has a high reliability, the offset is stored in memory as reference data for subsequent images that can only provide offsets with low reliability.

An example of a method for evaluating full-image offset reliability will be described with references to FIG. 12.

FIGS. 12 show curves 80 and 84 which track the variations in offsets in the comparative inspection device. In the figure, the horizontal axis represents the number of inspections and the vertical axis represents offset value. The reliability of a calculated offset can be evaluated by examining the relationship between the calculated offset position and the curve formed by the past offsets in the curve. For example, curve 80 is an example where past offsets are plotted over time. Due to cyclic vibration in the device or the like, the offsets show cyclic variations. In devices such as this one that show cyclic offset variations, the path of past offsets can be plotted to predict the current offset through extrapolation. In the figure, an offset 82 indicates the current predicted offset. If the offset that is actually calculated is close to predicted offset 82, the offset is inferred to have a high reliability. In one embodiment, an offset can be considered to be reliable if there is an error of no more than +/− a predetermined tolerance value, for example, 5%, between the actually calculated offset and the predicted offset 82. In this manner, calculated offsets can be evaluated more accurately by evaluating offset reliability through comparison with accumulated past offset values.

In the above description, the offset varies cyclically and prediction values are calculated through extrapolation. However, other methods can be used to calculate prediction values.

For example, as shown in FIG. 10 curve 84, only very recent offset values can be considered and the average of these values can be used as the prediction value. In the figure, an offset 86 is the average offset value. If the current measured offset is close to the offset 86, the measured offset can be evaluated as being correct. Regardless of the method used to calculate prediction values, the past offsets that are considered must have high reliability. Thus, if the offset calculated for the current alignment image has a high reliability, it is saved as history data to be used for calculating subsequent prediction values.

Another example of a method for evaluating reliability is to use the pattern density of the alignment image. For example, since the offset error rate will be low if there are adequate patterns in the x direction and the y direction, these cases are determined to have a high reliability. One example of a method for measuring pattern density is to determine differentials in the x direction and the y direction for each image element in the full image. There are generally various types of operators for calculating differentials. One example will be described with references to FIG. 13.

Figure 13:
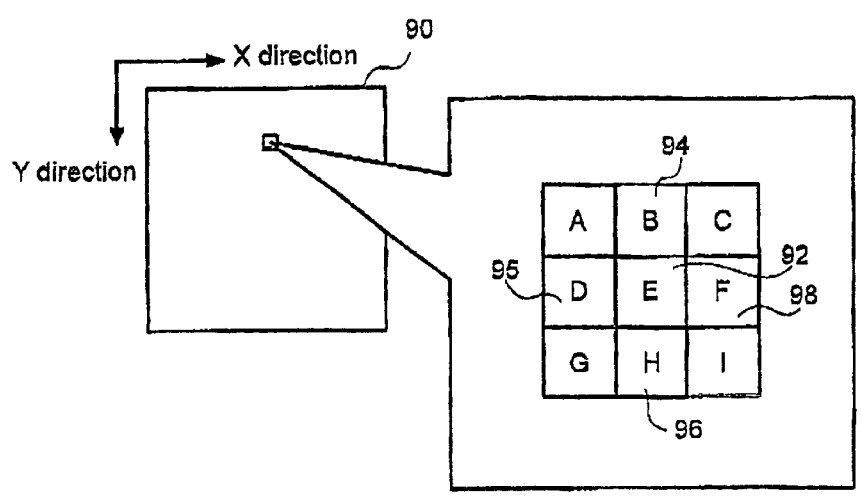
FIG. 13 shows a schematic drawing of a chip describing an example of a method for calculating pattern density in a chip of an embodiment of the present invention.

FIG. 13 is a schematic diagram of an alignment image for the purpose of describing a method for calculating pattern density in a chip of an embodiment of the present invention. The figure shows an alignment image 90. An image element E 92 in the chip image 90 will be examined. Using adjacent values, for example, the signal amplitude values for image elements B 94, D 95, F 98, and H 96, i.e., v(B), v(D), V(F), and v(H), the following calculations are performed.

Differential in signal value in the x direction at $E=(v(B)+v(H)-2\times v(E))$

Differential in signal value in the y direction at $E=(v(D)+v(F)-2\times v(E))$

Then, an evaluation is made based on the proportion (e.g., 10% or higher) of image elements having values greater than a predetermined threshold value relative to the total number of image elements.

Also, reliability can be evaluated using a combination of multiple combinations, e.g., evaluating using both comparisons with past offset values and current image pattern densities.

By checking reliability in this manner, the alignment precision based on calculated offsets can be monitored using a computer to see if positional alignment is performed correctly. If alignment precision is determined to be bad, a high possibility of detection error due to alignment error is assumed and the detection sensitivity is lowered beforehand.

If, for example, alignment precision is monitored based on pattern density, images with low densities will, of course, have low alignment reliability. However, if a pattern contains no patterns at all, for example, there is a high probability that an offset is mistakenly determined to be accurate, and there will be no detection error even if alignment takes place with a faulty offset. Similarly, detection errors will not take place when the image region contains only patterns in a specific direction, such as in FIG. 3 image 148. Therefore, in this embodiment, if alignment precision is found to be bad, an evaluation is made to determine if the failed alignment is critical for that image, i.e., if it will lead to a detection error.

In one embodiment, edge information, both direction and value, is checked for each channel, if it is above a fixed threshold. If it is, then the feature is critical. In FIG. 1 image 112, for example, if there is a misalignment in the vertical direction, then there is a high probability that a horizontal feature 23 will give a false defect reading. Thus, horizontal feature 23 is critical and detection sensitivity may be lowered. However, for vertical feature 22 a change in the vertical direction is unlikely to produce a false defect reading. Thus vertical feature 22 is not critical, i.e., a failed alignment is acceptable and the detection sensitivity is not lowered. By determining the criticality for a particular image in this manner, needless reductions in detection sensitivity are avoided. By accurately monitoring alignment precision and determining criticality of alignment errors in the current image, detection sensitivity can be reliably reduced when necessary to reduce detection errors (false positives) while also keeping the reductions of detection sensitivity to the necessary minimum. This makes high-sensitivity inspection possible over a wider range.

The description above presents an example where an embodiment of an image alignment method, a comparative inspection device, and an alignment precision monitoring method according to an embodiment of the present invention are implemented for a bright field inspection device for semiconductor wafers. However, the present invention can also be implemented for aligning comparison images in electron beam pattern inspection systems and DUV inspection systems.

Also, the inspected object is not restricted to semiconductor wafers, and anything for which defect detection is performed through image comparison can be used. For example, the present invention can be used for TFT substrates, photomasks, printed plates, and the like.

In order to overcome the problems of the conventional inspection technology, one embodiment of the present invention as described above provides a comparative inspection that compares an inspection image and a reference image and detects defects based on the difference between these images. The two images being compared are each divided into multiple regions, and offsets are calculated for each of the smaller regions. Of the calculated offsets, only the ones with high reliability are used to calculate an offset for the entire image. Thus, a high-precision alignment technology that is not dependent on pattern density or shape can be provided.

This also allows a highly sensitive comparative inspection method and device that reduces detection errors caused by alignment errors to be provided. Also, by monitoring alignment precision and reducing inspection sensitivity only when there is failed alignment, the reduction of detection sensitivity can be kept to the necessary minimum, and a highly sensitive comparative inspection method and device can be provided.

One specific embodiment of the present invention provides alignment precision in some cases of about 1 image element, and more specifically in some cases, 0.1 image element or less, and a rate of detection error caused by alignment errors of less than 10%, and more specifically in some case less than 1%, regardless of pattern density or shape and even when the comparison images are degraded.

Although the above functionality has generally been described in terms of specific hardware and software, it would be recognized that the invention has a much broader range of applicability. For example, the software functionality can be further combined or even separated. Similarly, the hardware functionality can be further combined, or even separated. The software functionality can be implemented in terms of hardware or a combination of hardware and software. Similarly, the hardware functionality can be implemented in software or a combination of hardware and software. Any number of different combinations can occur depending upon the application.

Many modifications and variations of the present invention are possible in light of the above teachings. Therefore, it is to be understood that within the scope of the appended claims, the invention may be practiced otherwise than as specifically described.

What is claimed is:

1. A comparative inspection device comprising:
   a stage on which an object is mounted and which moves said object;
   a detector for detecting an image of said object on said stage, said image comprising a plurality of inspection image regions, and for outputting an image signal;
   an image processing unit for receiving said image signal, determining a plurality of offsets for said plurality of inspection image regions relative to a plurality of corresponding reference image regions, and determining a selected offset out of a set of offsets of the plurality of offsets, wherein said set has at least one high reliability offset of said plurality of offsets
   a comparing unit for aligning an inspection image and a reference image using said selected offset and comparing said aligned inspection image and said reference image to detect a defect candidate; and
   a feature extracting unit for extracting a feature of said defect candidate.

2. The comparative inspection device of claim 1, wherein said plurality of corresponding reference image regions are related to a time delayed plurality of inspection image regions, wherein said inspection image is an entire image of said object.

3. The comparative inspection device of claim 1, wherein said selected offset is used to align an entire inspection image and an entire reference image.

4. The comparative inspection device of claim 1, wherein a reliability of an offset of said set is a high reliability offset if a pattern on an image region of said first image regions is dense and is a low reliability offset if said pattern is sparse.

5. The comparative inspection device of claim 1 wherein a reliability of an offset of said set is evaluated by comparing said offset with a predicted offset from past variations of offsets.

6. A comparative inspection device comprising:
   an image detection means for detecting a plurality of inspection image regions;
   an offset determining means for detecting offsets for said plurality of inspection image regions;
   an offset selection means for determining a selected offset with a high reliability from said offsets;
   an alignment means for aligning an entire inspection image and an entire reference image using said selected offset; and
   a comparing means for comparing said aligned inspection image and said reference image to detect a defect candidate; and
   a feature extracting unit for extracting a feature of said defect candidate.

7. A method for comparative inspection, said method comprising:
   detecting a first image of a specimen;
   detecting a second image of a specimen;
   dividing said first image into a plurality of divisional images;
   dividing said second image into a plurality of corresponding divisional images;
   calculating offsets between said plurality of divisional images and said plurality of corresponding divisional images;
   determining an offset between said first image and said second image out of a set of offsets between said calculated offsets;
   aligning said first image and said second image using said selected offset; and
   comparing said aligned first image and said second image to detect a defect candidate.

8. A method according to the claim 7 wherein, when images are received consecutively, full-image offset reliability of said image offset for said first image is evaluated and, if said full-image offset reliability is low, said first image is aligned using a past offset having a high full-image offset reliability.

9. A method according to the claim 7 wherein, when images are received consecutively, if an evaluation of full-image offset reliability for said image offset determines that full-image offset reliability is high, said image offset is stored as reference data for subsequent image alignments.

10. A method according to the claim 7 wherein, when images are received consecutively, full-image offset reliability is determined by comparing collected past offsets with high full-image offset reliability with said image offset.

11. A method according to the claim 7 wherein when images are received consecutively, full-image offset reliability of said image offset for said first image is evaluated and, if said full-image offset reliability is low, said first image is aligned using a past offset having a high full-image offset reliability.

12. A method for detecting defects in a semiconductor device, said method comprising:
   dividing an inspection image of said semiconductor device obtained by capturing an image of said semiconductor device into a plurality of inspection sub-images;
   dividing a reference image of said semiconductor device obtained by capturing an image of said semiconductor device into a plurality of corresponding sub-images each of which correspond to one of said inspection sub-images;
   forming a plurality of sub-image sets, each sub-image set comprising one of said inspection sub-images and a corresponding one of said corresponding sub-images;
   calculating a plurality of offsets for said plurality of sub-image sets;
   determining an image offset between said inspection image and said reference image from said calculated plurality of offsets;
   aligning said inspection image and said reference image using said determined image offset; and
   comparing said aligned inspection image and said reference image to detect a defect candidate.

13. A method according to the claim 12 wherein an offset of said plurality of offsets is determined using a correlation matrix for a sub-image set of said plurality of sub-image sets.

14. A method according to the claim 13 wherein said offset is a selected offset when said correlation matrix has a largest value above a predetermined threshold.

15. A method according to the claim 12 wherein said determining said image offset using selected offsets, comprises using correlation matrices associated with said selected offsets to determine a composite correlation matrix, and using said composite correlation matrix to determine said image offset.

16. A method according to the claim 12, further comprising extracting a feature of said defect candidate.

17. A comparative inspection device of a specimen on which a pattern is formed, said device comprising:

a detector, for receiving a current image of said pattern formed on said specimen;

an image processing unit for receiving a current image of said pattern from said detector and determining an offset between said current image and a corresponding previously-detected from a plurality of offset information between plural portions of said current image and a plural portions of said corresponding previously-detected image; and a defect inspection unit which aligns said current image and said corresponding previously-detected image by using said determined offset and compares said aligned current image and said corresponding previously-detected image to detect difference between said aligned current image and said corresponding previously-detected image as a defect.

18. A comparative inspection device according to the claim 17 wherein said offset is used in determining an alignment offset between said current image and said corresponding previously-detected image.

19. The comparative inspection device of claim 17, further comprising a delay memory for storing said corresponding portion.

20. A comparative inspection device according to the claim 17, further comprising a feature extracting unit for extracting a feature of said detected defect.

* * * * *